(12) United States Patent
Shin et al.

(10) Patent No.: US 9,517,383 B2
(45) Date of Patent: Dec. 13, 2016

(54) METHOD OF DISPLAYING MULTIMEDIA EXERCISE CONTENT BASED ON EXERCISE AMOUNT AND MULTIMEDIA APPARATUS APPLYING THE SAME

(71) Applicant: Samsung Electronics Co. Ltd., Suwon-si, Gyeonggi-do (KR)

(72) Inventors: Dong-yun Shin, Yongin-si (KR); Giu-yeol Kim, Suwon-si (KR); Du-seok Kim, Yongin-si (KR); Jun-mo Yang, Seoul (KR); Seung-youl Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 88 days.

(21) Appl. No.: 13/866,705

(22) Filed: Apr. 19, 2013

(65) Prior Publication Data

US 2013/0282157 A1    Oct. 24, 2013

(30) Foreign Application Priority Data

Apr. 20, 2012    (KR) .................. 10-2012-0041703

(51) Int. Cl.
*A63B 24/00* (2006.01)
*A63B 71/06* (2006.01)
*G06F 19/00* (2011.01)

(52) U.S. Cl.
CPC ....... *A63B 24/0062* (2013.01); *A63B 71/0622* (2013.01); *G06F 19/3481* (2013.01); *A63B 2024/0012* (2013.01); *A63B 2024/0015* (2013.01); *A63B 2071/0638* (2013.01); *A63B 2071/0644* (2013.01)

(58) Field of Classification Search
CPC ............ A63B 71/0622; A63B 71/0644; A63B 71/0638; A63B 24/00; A63B 2024/009; A63B 24/0062; G06F 19/3481
USPC .......................................... 482/1–8
See application file for complete search history.

(56) References Cited

U.S. PATENT DOCUMENTS

| 5,524,637 | A |   | 6/1996  | Erickson |
|-----------|---|---|---------|----------|
| 5,645,513 | A | * | 7/1997  | Haydocy et al. ............... 482/57 |
| 5,667,459 | A | * | 9/1997  | Su ..................... 482/4 |
| 5,888,172 | A | * | 3/1999  | Andrus et al. .................... 482/7 |
| 6,004,243 | A | * | 12/1999 | Ewert .............. 482/8 |
| 6,142,913 | A |   | 11/2000 | Ewert |
| 6,152,856 | A | * | 11/2000 | Studor et al. .................... 482/8 |

(Continued)

FOREIGN PATENT DOCUMENTS

| JP | 11-128394 A | 5/1999 |
| JP | 2007-144107 | 6/2007 |

(Continued)

*Primary Examiner* — Sundhara Ganesan
(74) *Attorney, Agent, or Firm* — Jefferson IP Law, LLP

(57) ABSTRACT

A display method and a multimedia apparatus applying the same are provided. The display method includes acquiring exercise information of a user, transmitting the exercise information to a server, receiving from the server a transport stream including video data in which a screen is changed at a rate corresponding to the exercise information, and displaying the video data by processing the transport stream. Therefore, the multimedia apparatus provides active multimedia exercise content to the user using exercise information and physical information of the user.

18 Claims, 8 Drawing Sheets

(56) References Cited

U.S. PATENT DOCUMENTS

| | | | |
|---|---|---|---|
| 6,287,239 B1* | 9/2001 | Hernandez | 482/1 |
| 6,336,891 B1* | 1/2002 | Fedrigon et al. | 482/8 |
| 6,428,449 B1* | 8/2002 | Apseloff | 482/3 |
| 6,582,342 B2* | 6/2003 | Kaufman | 482/8 |
| 7,217,224 B2* | 5/2007 | Thomas | 482/8 |
| 7,645,212 B2* | 1/2010 | Ashby et al. | 482/8 |
| 7,951,044 B1* | 5/2011 | Burks | 482/1 |
| 7,972,245 B2* | 7/2011 | Temple et al. | 482/8 |
| 2005/0239601 A1 | 10/2005 | Thomas | |
| 2006/0256076 A1 | 11/2006 | Liou et al. | |
| 2007/0190506 A1 | 8/2007 | Jeng et al. | |
| 2007/0219059 A1 | 9/2007 | Schwartz et al. | |
| 2010/0035726 A1* | 2/2010 | Fisher | A63B 24/0084 482/8 |
| 2010/0146078 A1 | 6/2010 | Wolff et al. | |
| 2010/0279822 A1 | 11/2010 | Ford | |
| 2011/0007018 A1 | 1/2011 | McKinley et al. | |
| 2011/0195383 A1 | 8/2011 | Weiss | |

FOREIGN PATENT DOCUMENTS

| | | |
|---|---|---|
| KR | 10-2002-0006880 A | 1/2002 |
| KR | 10-2002-0078077 A | 10/2002 |
| KR | 10-2007-0018366 A | 2/2007 |
| KR | 10-2007-0064053 A | 6/2007 |
| KR | 10-2009-0015773 A | 2/2009 |
| KR | 10-2009-0077224 A | 7/2009 |
| KR | 10-2012-0010398 A | 2/2012 |
| KR | 10-2013-0031469 A | 3/2013 |

* cited by examiner

US 9,517,383 B2

METHOD OF DISPLAYING MULTIMEDIA EXERCISE CONTENT BASED ON EXERCISE AMOUNT AND MULTIMEDIA APPARATUS APPLYING THE SAME

PRIORITY

This application claims the benefit under 35 U.S.C. §119(a) of a Korean patent application filed on Apr. 20, 2012 in the Korean Intellectual Property Office and assigned Serial No. 10-2012-0041703, the entire disclosure of which is hereby incorporated by reference.

BACKGROUND OF THE INVENTION

1. Field of the Invention

The present invention relates to apparatuses and methods consistent with exemplary embodiments related to a display method and a multimedia apparatus applying the same. More particularly, the present invention relations to a display method of controlling reproduction of multimedia exercise content based on exercise information and physical information of a user and a multimedia apparatus applying the same.

2. Description of the Related Art

With a growth in the aging population as well as with an increase of obese people, the concern for health care is increased. In recent years, programs which care for the health of a user using a personal terminal have increased. For example, health care programs and applications which periodically manage health information and exercise information of a user have been developed.

In particular, the user enjoys exercise contents with various multimedia apparatuses to exercise more effectively. For example, the user can run or play golf using a large screen, or can run or perform aerobics while listening to music.

However, in the related art, since exercise contents or music contents of a same pattern are provided regardless of an exercise amount performed by the user, the user is not comfortable exercising or becomes bored using the multimedia apparatuses.

In addition, although it is possible to reproduce exercise contents by taking into consideration the exercise amount of the user in the related art, the user's health information is not taken into consideration and thus a correct exercise routing is not provided to the user.

Therefore, there is a need for an apparatus and a method to more actively engage the user when exercising using the multimedia apparatuses.

SUMMARY OF THE INVENTION

Aspects of the present invention are to address at least the above-mentioned problems and/or disadvantages and to provide at least the advantages described above and others not described above. However, it is understood that one or more exemplary embodiments are not required to overcome the disadvantages described above, and may not overcome any of the problems described above. Accordingly, an aspect of the present invention is to provide a display method which controls a reproduction rate of multimedia exercise contents according to information for an exercise amount and physical information of a user and a multimedia apparatus using the same.

In accordance with an aspect of the present invention, a method of a multimedia apparatus is provided. The method includes acquiring exercise information of a user, transmitting the exercise information of the user to a server, receiving from the server a transport stream comprising video data in which a screen is changed at a rate corresponding to the exercise information, and displaying the video data by processing the transport stream.

The exercise information of the user may include an exercise speed and a screen change rate may be adjusted in proportion to the exercise speed.

The method may further include storing physical information of the user, determining a recommended exercise criterion corresponding to the physical information of the user, comparing the exercise information of the user with the recommended exercise criterion when the exercise information of the user is acquired, and displaying a guidance message for the recommended exercise criterion when the exercise information of the user does not match the recommended exercise criterion.

The method may further include receiving from the server and displaying a guidance message for a recommended exercise criterion when the exercise information of the user does not match the recommended exercise criterion corresponding to the physical information of the user.

The transport stream further includes reference video data in which the screen is changed at a rate corresponding to recommended exercise criterion when the exercise information of the user does not match the recommended exercise criterion corresponding to physical information of the user, and processing the reference video data and displaying the video data.

The method may further include, outputting first audio data corresponding to the video data, and converting the first audio data into second audio data and outputting the second audio data when an exercise amount included in the exercise information exceeds a preset first threshold value.

The method may further include outputting a User Interface (UI) including a cheering message when an exercise amount included in the exercise information of the user exceeds a preset second threshold value.

The method may further include displaying a UI including the exercise information of the user together with the video data.

The method may further include outputting a UI including an exercise completion message when an exercise amount included in the exercise information of the user exceeds a preset third threshold value.

The server may be provided in the multimedia apparatus.

In accordance with another aspect of the present invention, a multimedia apparatus is provided. The multimedia apparatus includes an exercise information acquisition unit configured to acquire exercise information of a user, a communication unit configured to perform communication with a server, a display unit, and a control unit configured to control the communication unit to transmit the exercise information of the user to the server and to receive from the server a transport stream including video data in which a screen is changed at a rate corresponding to the exercise information of the user, and to control the display unit to display the video data by processing the transport stream.

The exercise information of the user may include an exercise speed and a screen change rate may be adjusted in proportion to the exercise speed.

The multimedia apparatus may further include a storage unit configured to store physical information of the user. The control unit may determine a recommended exercise criterion corresponding to the physical information of the user, compare the exercise information of the user with the recommended exercise criterion when the exercise information of the user is acquired, and control a guidance message for the recommended exercise criterion to be displayed on the display unit when the exercise information of the user does not match the recommended exercise criterion.

The control unit may receive a guidance message for the recommended exercise criterion from the server through the communication unit when the exercise information of the user does not match the recommended exercise criterion corresponding to physical information of the user, and the control unit may control the received guidance message to be displayed on the display unit.

The transport stream further includes reference video data in which the screen is changed at a rate corresponding to a recommended exercise criterion when the exercise information of the user does not match the recommended exercise criterion corresponding to the physical information of the user, and the control unit may further control the received reference video data to be processed and the processed reference video data to be displayed on the display unit.

The multimedia apparatus may further include an audio output unit configured to output first audio data corresponding to the video data. The control unit may control the audio output unit to convert the first audio data into second audio data and output the second audio data when an exercise amount included in the exercise information of the user exceeds a preset first threshold value.

The control unit may output a UI including a cheering message when an exercise amount included in the exercise information of the user exceeds a preset second threshold value.

The control unit may control a UI including the exercise information of the user to be displayed on the display unit together with the video data.

The control unit may output a UI including an exercise completion message when an exercise amount included in the exercise information of the user exceeds a preset third threshold value.

The server may be provided in the multimedia apparatus.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taking in conjunction with the accompanying drawings, in which.

Throughout the drawings, it should be noted that like reference numbers are used to depict the same or similar elements, features, and structures.

DETAILED DESCRIPTION OF EXEMPLARY EMBODIMENTS

Figure 1:
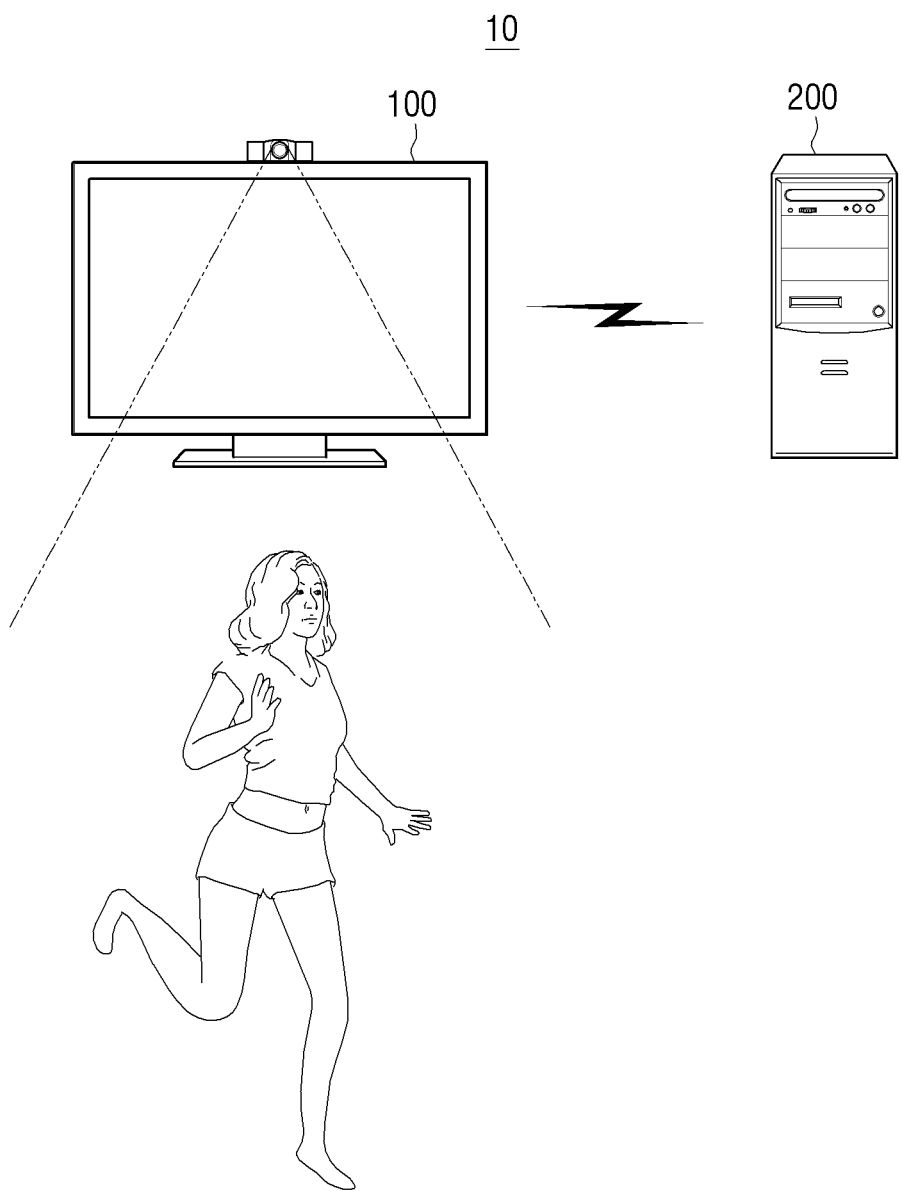
FIG. 1 is a view illustrating a system for providing a multimedia exercise content according to an exemplary embodiment of the present invention.

Hereinafter, exemplary embodiments will be described in more detail with reference to the accompanying drawings.

In the following description, same reference numerals are used for the same elements when they are depicted in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, functions or elements known in the related art are not described in detail since they would obscure the exemplary embodiments with unnecessary detail.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural references unless the context clearly dictates otherwise. Thus, for example, reference to "a component surface" includes reference to one or more of such surfaces.

FIG. 1 is a view illustrating a system for providing multimedia exercise content according to an exemplary embodiment of the present invention.

Referring to FIG. 1, a system 10 for providing a multimedia exercise content includes a multimedia apparatus 100 and a multimedia exercise content providing server 200 (hereinafter, referred to as server) connected to the multimedia apparatus 100. The multimedia apparatus 100 may be a TeleVision (TV) as shown in FIG. 1, but it is noted that this is merely one example. The multimedia apparatus 100 may include a multimedia apparatus such as a computer, a Personal Digital Assistant (PDA), a mobile phone, or the like.

The multimedia apparatus 100 receives multimedia exercise content from the server 200 and displays the received multimedia exercise content. The multimedia exercise content may include video data and audio data and may be received in a transport stream form.

The multimedia apparatus 100 acquires exercise information of a user. For example, the multimedia apparatus 100 may acquire the exercise information by tracing a motion of the user using a camera. Alternatively, the multimedia apparatus 100 may acquire the exercise information of the user using various sensors (for example, an acceleration sensor, a weight sensor, a blood pressure gauge, a pulsometer, or the like).

Herein, the exercise information may include any one of an exercise amount (e.g., a caloric value), an exercise period, an exercise speed, and an exercise distance. However, it is noted that these are merely some examples, and the exercise information may include various other types of exercise information such as a pulse rate and change in weight.

The multimedia apparatus 100 transmits the acquired exercise information to the external server 200.

The server 200 adjusts a screen change rate of video data included in the multimedia exercise content according to the received exercise information. Specifically, the server 200 processes the video data to increase the screen change rate of the video data when an exercise amount of the user is large, while the server 200 processes the video data to reduce the screen change rate of the video data when the exercise amount of the user is small. However, this is merely an exemplary embodiment and the screen change rate of the video data can change in various other forms.

The server 200 may adjust the screen change rate of the video data included in the multimedia exercise content according to physical information of the user. For example, the server 200 receives the physical information (such as age, weight, sex, basic exercise capacity, and the like) of the user from the user. When the server 200 acquires the exercise information from the user, the server 200 compares the exercise information with a recommended exercise criterion corresponding to the physical information of the user. When the exercise information does not match the recommended exercise criterion, the server 200 generates a transport stream including reference video data in which a screen is changed at a rate corresponding to the recommended exercise criterion. For example, when the input exercise information is equal to or less than a preset value with respect to the recommended exercise criterion, the server 200 increases a screen change rate of current video data and generates video data. When the input exercise information exceeds the preset value with respect to the recommended exercise criterion, the server 200 reduces the screen change rate of the current video data and generates video data.

The server 200 may control reproduction of the multimedia exercise content according to the received exercise information of the user. For example, when the exercise information, which is equal to or larger than a preset first threshold value, is received from the multimedia apparatus 100, the server 200 may execute the multimedia exercise content. When the exercise information, which is equal to or larger than a preset second threshold value, is received from the multimedia apparatus 100, the server 200 may stop executing the multimedia exercise content.

The server 200 may add various User Interfaces (UIs) to the multimedia exercise content according to the received exercise information of the user. For example, when the exercise information, which is equal to or larger than a specific value, is received from the multimedia apparatus 100, the server 200 may add a UI including the exercise information, a UI including a guidance message corresponding to the recommended exercise criterion, a UI including a cheering message, and a UI including an exercise completion message to the multimedia exercise information.

The server 200 transmits a transport stream including video data of which the screen change rate is adjusted and to which the various UIs are added to the multimedia apparatus 100.

The multimedia apparatus 100 receives the transport stream including the video data of which the screen change rate is adjusted, and processes the received transport stream.

The multimedia apparatus 100 displays the video data included in the transport stream to be provided to the user.

The server 200 and the multimedia apparatus 100 iteratively perform the above-described operations until the multimedia exercise content is completed (for example, until the user inputs a completion command, or until the exercise amount exceeds a preset value). When the multimedia exercise content is completed, the above-described operation is completed.

As described above, since the multimedia apparatus 100 provides the multimedia exercise content including the video data of which the screen change rate is adjusted according to the exercise information in a real time, it is possible for the multimedia apparatus 100 to provide active and lively multimedia exercise content to the user.

Hereinafter, the multimedia apparatus 100 according to an exemplary embodiment will be described with reference to FIGS. 2 and 3.

Figure 2:
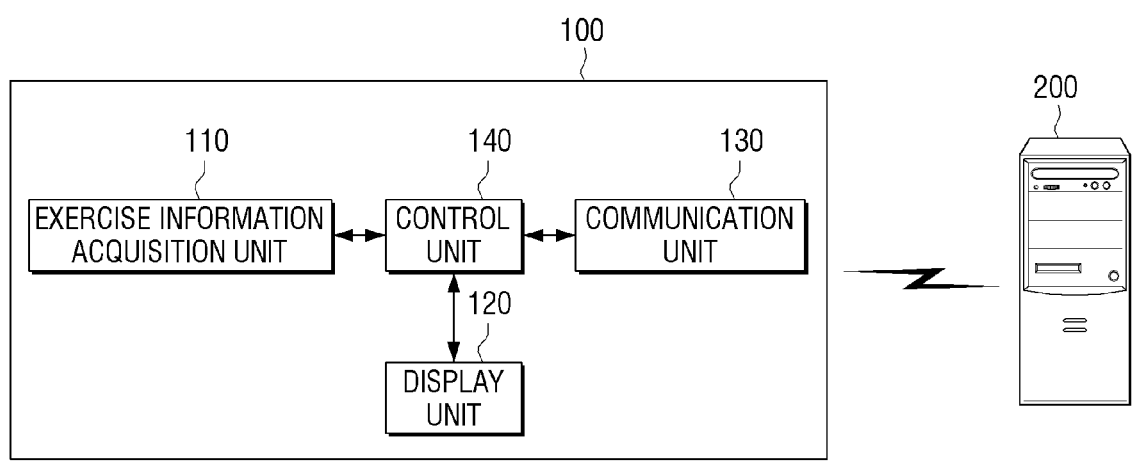
FIG. 2 is a schematic block diagram illustrating a configuration of a multimedia apparatus according to an exemplary embodiment of the present invention.

FIG. 2 is a schematic block diagram illustrating a configuration of the multimedia apparatus according to an exemplary embodiment.

Referring to FIG. 2, the multimedia apparatus 100 includes an exercise information acquisition unit 110, a display unit 120, a communication unit 130, and a control unit 140.

The exercise information acquisition unit 110 may acquire exercise information from a motion of the user. Specifically, the exercise information acquisition unit 110 may capture the motion of the user using a camera, analyze the captured motion of the user, and acquire the exercise information of the user.

The exercise information acquisition unit 110 may acquire information for a specific portion of a body of the user according to the multimedia exercise content. For example, when a kind of the multimedia exercise content is running, the exercise information acquisition unit 110 may capture only legs of the user to acquire the exercise information. When the kind of the multimedia exercise content is swimming, the exercise information acquisition unit 110 may capture the legs and hands of the user to acquire the exercise information.

The exercise information acquisition unit 110 may acquire the exercise information of the user using various sensors. For example, the exercise information acquisition unit 110 may acquire motion information of the user using an acceleration sensor and the like, and physical information of the user using a pulsometer and the like.

The display unit 120 displays video data of the multimedia exercise content received from the server 200.

The communication unit 130 performs communication with the external server 200. The communication unit 130 may transmit the exercise information and physical information of the user to the server 200, and receive multimedia exercise content of a transport stream form from the server 200.

The control unit 140 controls the multimedia apparatus 100 according to the user's operation. The control unit 140 processes the transport stream including the multimedia exercise content received from the server 200, and controls the display unit 120 to display video data.

The control unit 140 may generate and display various UIs according to the exercise information of the user. For example, when the exercise information does not match the recommended exercise criterion, the control unit 140 may display a UI including a guidance message for guiding exercise information corresponding to the recommended exercise criterion. When an exercise amount exceeds a preset second threshold value, the control unit 140 may display a UI including a cheering message. When the exercise amount exceeds a preset third threshold value, the control unit 140 may display a UI including an exercise completion message. The control unit 140 may display the exercise information acquired by the exercise information acquisition unit 110 together with the video data of the multimedia exercise content.

In the above-described exemplary embodiment, directly generating UIs in the multimedia apparatus 100 has been described, but this is merely an example. The multimedia apparatus 100 may receive a transport stream in which the UI is added to the video data of the multimedia exercise content from the external server 200, process the received transport stream, and display the process result.

As described above, the example in which the multimedia apparatus 100 receives the multimedia exercise content from the server 200 and outputs the received multimedia exercise content has been described, but this is merely an example. The multimedia apparatus 100 may have the function of the server 200 to directly execute the multimedia exercise content.

Specifically, when the exercise information acquisition unit 110 acquires the exercise information while the multimedia apparatus 100 executes the multimedia exercise content, the control unit 140 may adjust the screen change rate of the video data included in the multimedia exercise content according to the exercise information. For example, the control 140 may process the multimedia exercise content to increase the screen change rate of the video data when the exercise amount is large, while the control 140 may process the multimedia exercise content to reduce the screen change rate of the video data when the exercise amount is small.

The control unit 140 may determine the recommended exercise criterion according to the physical information input by the user, and compare the exercise information with the recommended exercise criterion when the exercise information is acquired. The recommended exercise criterion may be calculated based on the physical information (for example, age, weight, height, sex, and the like) and health-related information (for example, basic physical strength information, disease presence/absence, and the like) of the user.

The control unit 140 may control a guidance message for the recommended exercise criterion to be displayed on the display unit 120 when the exercise information does not match the recommended exercise criterion.

The control unit 140 may adjust the screen change rate of the video data included in the multimedia exercise content to be matched with the recommended exercise criterion when the exercise information does not match the recommended exercise criterion. When the input exercise information is equal to or less than a preset value with respect to the recommended exercise criterion, the control unit 140 may processes the multimedia exercise content to increase a screen change rate of currently output video data. When the input exercise information exceeds the preset value with respect to the recommended exercise criterion, the control unit 140 may processes the multimedia exercise content to reduce the screen change rate of the currently output video data.

The multimedia apparatus 100 according to the above-described various exemplary embodiments can provide lively and active multimedia exercise content to the user using the exercise information and physical information of the user.

Figure 3:
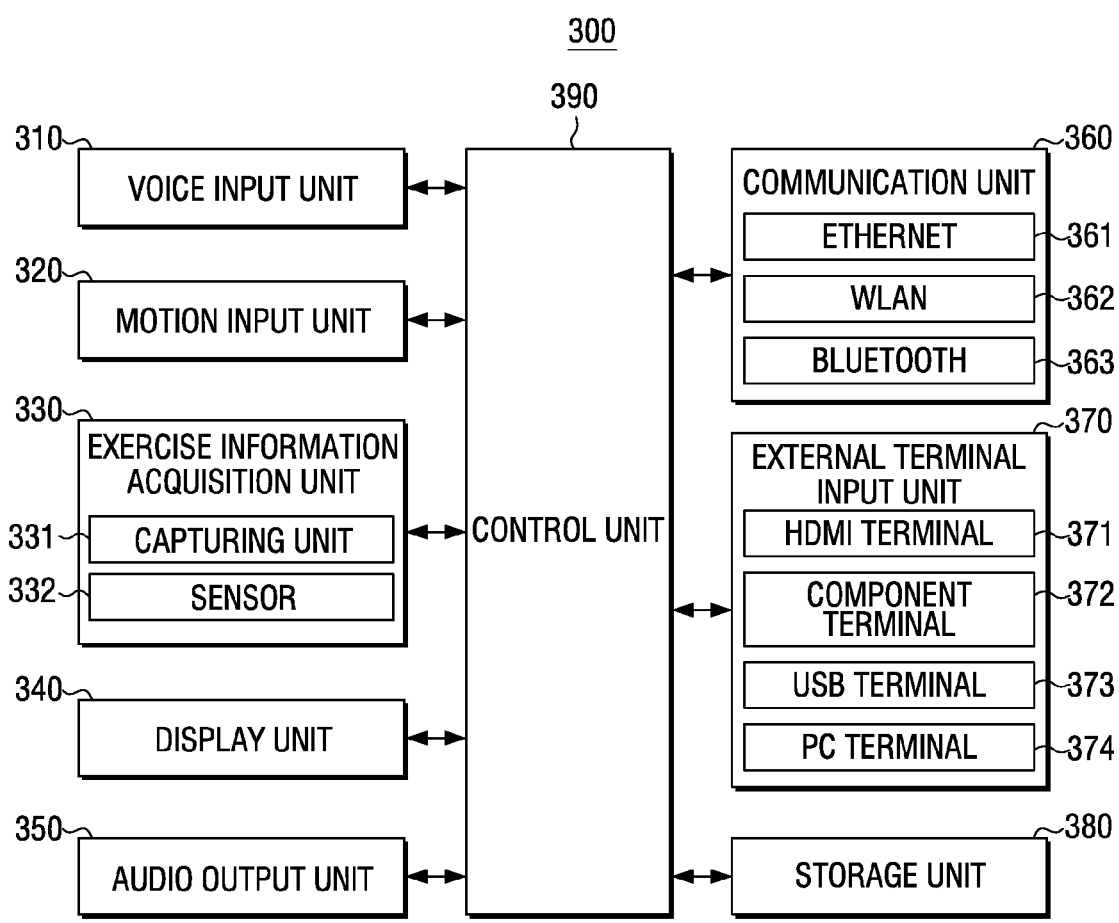
FIG. 3 is a detailed block diagram illustrating a configuration of a multimedia apparatus according to an exemplary embodiment of the present invention.

FIG. 3 is a detailed block diagram illustrating a configuration of a multimedia apparatus according to an exemplary embodiment.

Referring to FIG. 3, the multimedia apparatus 300 includes a voice input unit 310, a motion input unit 320, an exercise information acquisition unit 330, a display unit 340, an audio output unit 350, the communication unit 360, an external terminal input unit 370, a storage unit 380, and a control unit 390.

A description of the exercise information acquisition unit 330, the display unit 340, the communication unit 360, and the control unit 390 is the same as that of the exercise information acquisition unit 110, the display unit 120, the communication unit 130, and the control unit 140, which have been described with reference to FIG. 2, and thus will be omitted herein for brevity.

The voice input unit 310 receives voice uttered by the user to recognize the voice. The voice input unit 310 converts the input voice signal into an electrical signal and outputs the converted electrical signal to the control unit 390. The control unit 390 detects start and end of the voice uttered by the user in the voice signal input from the user to determine a voice section. The control unit 390 may calculate energy of the input voice signal, classify an energy level of the voice signal according to the calculated energy, and detect the voice section through dynamic programming. The control unit 390 detects a phoneme, which is minimum units of a voice, from a voice signal within the detected voice section based on an acoustic model and generates phoneme data. The control unit 390 generates text information by applying a Hidden Markov Model (HMM) probability model to the generated phoneme data. Therefore, the control unit 390 may recognize the voice of the user included in the voice signal.

The motion input unit 320 receives a video signal captured by the user and provides the captured video signal to the control unit 390 to perform motion recognition. The control unit 390 may recognize motion taken by the user using a motion recognition module stored therein. Specifically, the control unit 390 controls the input video signal to be stored in frame units. The control unit 390 compares a plurality of stored frames with each other to detect a portion in which the motion is preset. That is, the control unit 390 divides each frame into a plurality of blocks and then detects a representative value (an average pixel value, a maximum pixel value, a minimum pixel value, and the like) of each of the plurality of blocks. Thereby, when blocks having the representative value within a constant range are consecutively arranged, the corresponding blocks may be recognized to form one object. Further, the control unit 390 may recognize a shape of a corresponding object by grasping connection states of the blocks, and a color of the block by checking pixel values of the blocks. For example, hands, a face, a specific object, and the like of the user may be recognized as one object. When an object is recognized, the control unit 390 checks positions of the object from a previous frame and a current frame, and determines whether or not the object moves. Therefore, when the user makes a motion in which the user grasps and shakes hands or the specific object, the control unit 390 may recognize the hands or the specific object of the user, that is, recognize the motion of the object.

The control unit 390 may trace a motion of a portion which has been detected as the object. At this time, the control unit 390 may predict the motion of the object, and remove noise included in an area other than a motion-predicted area of the object. The control unit 390 determines the motion of the user according to a shape and a position of the traced object. Specifically, the control unit 390 determines change in shape, speed, position, direction, and the like of the object and then determines whether the motion of the user is grabbing, point-moving, slapping, shaking, or rotating.

The exercise information acquisition unit 330 detects motion information of the user to acquire exercise information. At this time, the exercise information acquisition unit 330 may include a capturing unit 331 and a sensor 332 as shown in FIG. 3.

Hereinafter, a method of measuring exercise information by the exercise information acquisition unit 330 using the capturing unit 331 and the sensor 332 will be described.

First, the exercise information acquisition unit 330 may map a sample motion image with an exercise amount using a Metabolic Equivalent of Task (METs) and store the mapping result. At this time, METs is one of units representing an exercise intensity and indicates an oxygen amount required to maintain a stable state. In particular, METs values for the general motions have been pre-defined, for example, walking 3 km per hour is 2 METs and jogging 9 km per hour is 8 METs. The METs values for general motions of the user are listed in the following Table 1.

TABLE 1

| Motion of User | METs value |
| --- | --- |
| Sleeping | 0.9 |
| Sitting | 1.0 |
| Lining up | 1.2 |
| Dishwashing | 2.3 |
| Ironing | 2.3 |
| Stretching | 2.5 |
| Walking | 3.0 |
| Vacuum-cleaning | 3.5 |
| Drumming | 4.0 |
| Badminton | 4.5 |
| Baseball | 5.0 |
| Aerobic | 6.5 |
| Soccer | 7.0 |
| Jogging | 8.0 |
| Biking (fast) | 10.0 |
| Running | 15.0 |

The exercise information acquisition unit 330 selects a sample motion to be modeling among the motions defined in METs according to the user's command. When a sample motion image for the selected sample motion is acquired through the capturing unit 331, the exercise information acquisition unit 330 performs modeling on the sample motion of the user using the sample motion image. Specifically, the exercise information acquisition unit 330 may measure change in (x, y, z) coordinates of a plurality of points (for example, 14 points) of the user's body for a preset time (for example, one second), and perform modeling on the sample motion of the user.

The exercise information acquisition unit 330 acquires a value of an exercise amount for the sample motion selected using the METs value for the general motion of the user. Specifically, the exercise information acquisition unit 330 may acquire the value of the exercise amount corresponding to the motion defined in METs as the value of the exercise amount of the selected sample motion.

The exercise information acquisition unit 330 may map the sample motion image for the selected sample motion with the acquired value of the exercise amount and store the mapping result.

As described above, when the sample motion image and the information for the exercise amount are mapped and stored, the exercise information acquisition unit 330 acquires the motion image of the user through the capturing unit 331. At this time, the exercise information acquisition unit 330 may acquire the motion image using the capturing unit 331 such as a three-Dimensional (3D) camera or a depth camera.

The exercise information acquisition unit 330 calculates a motion similarity between the motion image and the sample motion image. Specifically, the exercise information acquisition unit 330 may divide the acquired motion image into a plurality of blocks, compare motions of coordinate values for the plurality of blocks of the acquired sample motion image with motions of coordinate values for the plurality of blocks of a pre-stored sample motion image, and then calculate the motion similarity. At this time, the plurality of blocks may include five blocks, that is, a left leg block, a right leg block, a left arm block, a right arm block, and a body block in the user's body. However, this is merely an example and the user's body may be divided into a plurality of blocks other than the five blocks described above.

In particular, there may be a plurality of pre-stored sample motion images, the exercise information acquisition unit 330 may wholly calculate the motion similarity between the motion image and each of the plurality of sample motion images.

The exercise information acquisition unit 330 calculates an exercise amount using the calculated motion similarity. At this time, when a motion corresponding to the motion image is the motion defined in METs, the exercise information acquisition unit 330 calculates a first exercise amount of METs units using the motion similarity with the sample motion image. The exercise information acquisition unit 330 may calculate a final exercise amount of calorie units using any one of an exercise period, a weight, sex information and age information of the user in addition to the first exercise amount.

However, the method of calculating an exercise amount described above is merely an example and the exercise amount of the user may be calculated using other methods. For example, the exercise information acquisition unit 330 may measure the exercise amount of the user using the various kinds of sensors. The exercise information acquisition unit 330 may measure the exercise amount of the user using a heart rate, a pulse rate, and the like.

The exercise information acquisition unit 330 may acquire various exercise information in addition to the above-described exercise amount. For example, the exercise information acquisition unit 330 may calculate an exercise period, an exercise speed, an expected exercise distance, and the like of the user and acquire various exercise information such as heart rate, pulse rate, change in weight, change in temperature, and the like.

The display unit 340 displays signal-processed video data. For example, the display unit 340 may display video data included in the multimedia exercise content received from the server 200.

The display unit 340 may display various UIs together with the multimedia exercise content. For example, the display unit 340 may display any one of a UI including the exercise information, a UI including a guidance message for guiding the recommended exercise criterion, a UI including a cheering message, and a UI including an exercise completion message together with the multimedia exercise content.

The audio output unit 350 outputs audio data by control of the control unit 390. In particular, the audio output unit 360 may output audio data included in the multimedia exercise content received from the server 200.

The audio output unit 360 may be implemented with a speaker, a headphone output terminal, a Sony/Philips Digital Interface (S/PDIF) output terminal, and the like.

The communication unit 360 may be connected to the external server 200 to communicate with the server 200 under control of the control unit 390. For example, the communication unit 360 may transmit exercise information and physical information of the user to the external server 200. In addition, the communication unit 360 may receive a multimedia exercise content including video data, of which a screen change rate is adjusted, from the server 200.

The communication unit 360 may be implemented with Ethernet 361, a Wireless Local Area Network (WLAN) 362, Bluetooth 363, and the like as shown in FIG. 3, but the communication unit 360 is not limited thereto.

The external terminal input unit 370 includes a High-Definition Multimedia Interface (HDMI) terminal 371, a component terminal 372, a Universal Serial Bus (USB) terminal 373, and a Personal Computer (PC) terminal 374. The external terminal input unit 370 may receive video data (for example, a moving image, a photo, and the like), audio data (for example, music, and the like), and control data (for example, reproduction command, and the like) from an external apparatus.

The storage unit 380 may store various data and programs used to drive the multimedia apparatus 300. In particular, the storage unit 380 may store various software modules such as a power control module, a voice recognition module, a motion recognition module, an exercise information acquisition module, and a UI generation module.

In particular, the storage unit 380 may store the exercise information and physical information of the user acquired from the exercise information acquisition unit 330. In addition, the storage unit 380 may store basic physical strength information and health-related information input by the user.

The control unit 390 controls the multimedia apparatus 300 according to the user's command. Specifically, the control unit 390 processes a transport stream including the multimedia exercise content received from the server 200 and controls the display 340 to display video data. The video data may include a background screen such as a trail, a strolling alley, or an 011e road to provide the same environment as an environment in which the user exercises.

In particular, the video data may have a screen change rate corresponding to the exercise information (for example, exercise speed) of the user. Specifically, the video data may have the screen change rate in proportion to the exercise speed of the user. For example, when the exercise speed of the user is gradually increased (for example, when the exercise speed of the user is fast, or when a calorie consumed per hour is large), the multimedia exercise content may include video data having a screen change rate faster than a current screen change rate. However, when the exercise speed of the user is gradually reduced (for example, when the exercise speed of the user is slow, or when a calorie consumed per hour is small), the multimedia exercise content may include video data having a screen change rate slower than the current screen change rate.

The screen change rate of the video data may be adjusted according to the physical information of the user. Specifically, the multimedia apparatus 300 or the server 200 receives the physical information (for example, age, weight, sex, basic exercise capacity, health-related information, and the like) of the user from the user. At this time, when the multimedia apparatus 300 receives the physical information of the user, the multimedia apparatus 300 may transmit the received physical information of the user to the server 200.

When the server 200 acquires the exercise information (for example, an exercise amount or exercise speed) from the user, the server 200 compares the exercise information with the recommended exercise criterion corresponding to the physical information of the user. At this time, the recommended exercise criterion may be determined based on the physical information (for example, age, weight, height, sex, basic exercise capacity, and health-related information of the user) of the user. For example, the recommended exercise criterion may be the highest in age 20s, may become increased closer to a standard weight, and may be higher in men than in women.

When the received exercise information does not match the recommended exercise criterion, the server 200 may generate a transport stream including reference video data in which a screen is changed at a rate corresponding to the recommended exercise criterion. For example, when the received exercise information is equal to or less than a preset value with respect to the recommended exercise criterion, the server 200 may increase a screen change rate of current video data to generate the reference video data. When the received exercise information exceeds the preset value with respect to the recommended exercise criterion, the server 200 may reduce the screen change rate of the current video to generate the reference video data.

Audio data of the multimedia exercise content may be adjusted to correspond to the exercise information like the video data. For example, when an exercise amount is included in a preset first range, first audio data may be included in the multimedia exercise content. When the exercise amount is included in a preset second range, second audio data may be included in the multimedia exercise content. At this time, lilting audio data of fast tempo may be included in the multimedia exercise content to encourage and cheer the user as the exercise amount is increased.

In the above-described exemplary embodiment, the example in which the audio data is music has been described, but the audio data may be a voice message such as cheer phrases. For example, when the exercise exceeds the preset value, the voice message such as "please cheer up" may be included in the audio data.

Further, various UIs may be generated according to the exercise information of the user and then displayed in the video data included in the multimedia exercise content.

Figure 4:
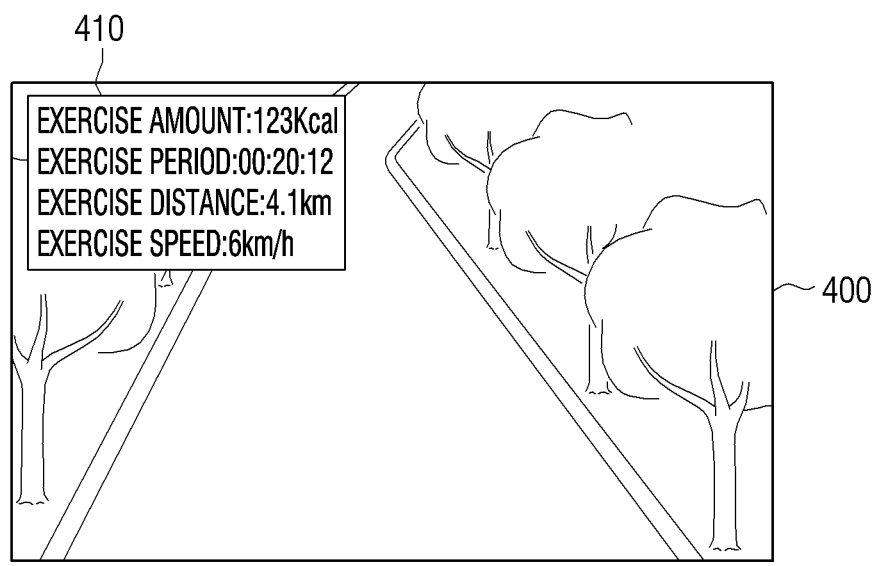
FIG. 4 is a view illustrating video data displayed in a multimedia apparatus according to an exemplary embodiment of the present invention.

FIG. 4 is a view illustrating video data displayed in a multimedia apparatus according to an exemplary embodiment of the present invention.

Referring to FIG. 4, a UI 410 including exercise information of the user may be generated in the video data included in the multimedia exercise content and displayed on the multimedia apparatus 400. The UI 410 including the exercise information of the user may include any one of an exercise amount, an exercise period, an exercise speed, and an exercise distance as shown in FIG. 4.

Figure 5:
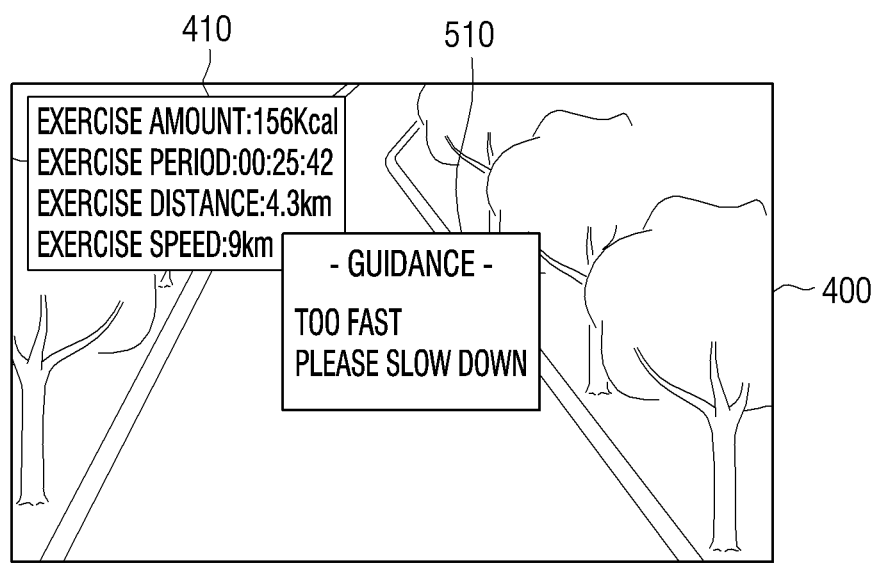
FIG. 5 is a view illustrating a User Interface (UI) including a guidance message for a recommended exercise criterion according to an exemplary embodiment of the present invention.

Further, when the exercise information does not match the recommended exercise criterion, the video data included in the multimedia exercise content may include a UI 510 including a guidance message for guiding exercise information corresponding to the recommended exercise criterion as shown in FIG. 5.

FIG. 5 is a view illustrating a UI including a guidance message for a recommended exercise criterion according to an exemplary embodiment of the present invention.

Referring to FIG. 5, when the exercise speed exceeds the recommended exercise criterion, the video data included in the multimedia exercise content may include the UI 510 including the guidance message such as "Too fast. Please slow down". However, the above-described guidance message included in the UI 510 is merely an example, and other guidance messages may be included in the UI 510.

Figure 6:
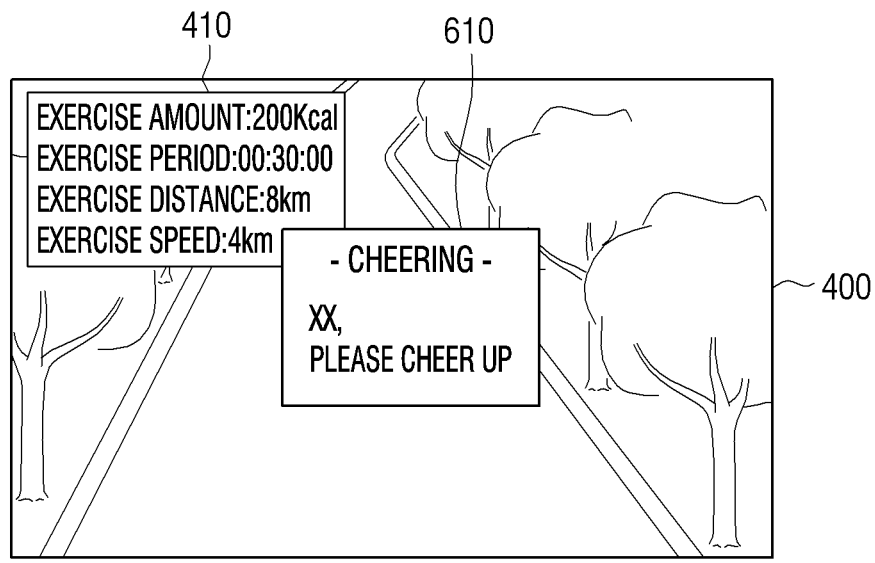
FIG. 6 is a view illustrating a UI including a cheering message according to an exemplary embodiment of the present invention.

When the exercise amount exceeds a preset second threshold value, the video data included in the multimedia exercise content may include a UI 610 including a cheering message as shown in FIG. 6.

FIG. 6 is a view illustrating a UI including a cheering message according to an exemplary embodiment of the present invention.

Referring to FIG. 6, the exercise amount of the user exceeds a first exercise amount (for example, 100 Kcal), the video data included in the multimedia exercise content may include the UI 610 including the cheer message such as "XX, cheer up". However, the cheer message included in the UI 610 is merely an example, and other cheering messages may be included in the UI 610.

Figure 7:
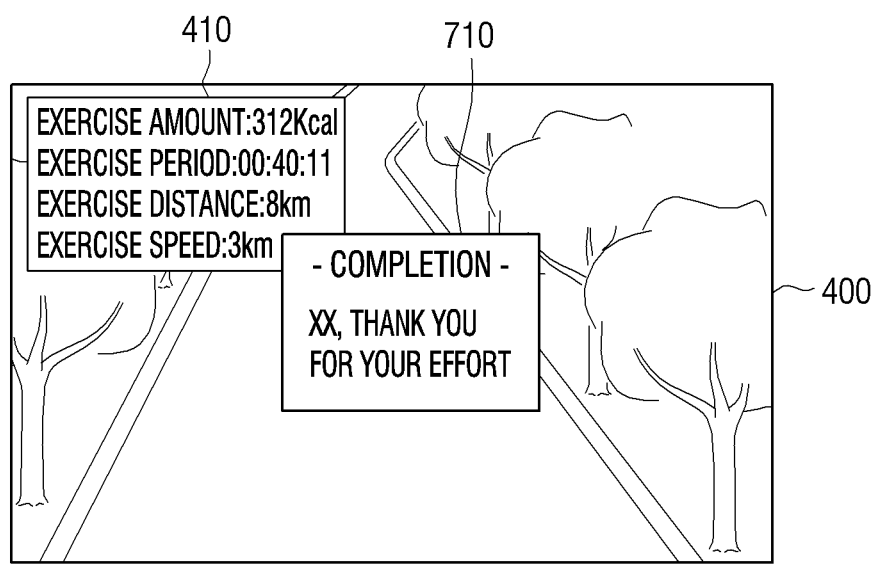
FIG. 7 is a view illustrating a UI including an exercise completion message according to an exemplary embodiment of the present invention.

When the exercise amount exceeds a preset third threshold value, the video data included in the multimedia exercise content may include a UI 710 including an exercise completion message as shown in FIG. 7.

FIG. 7 is a view illustrating a UI including an exercise completion message according to an exemplary embodiment of the present invention.

Referring to FIG. 7, when the exercise amount of the user exceeds a second exercise amount (for example, 200 Kcal), the video data included in the multimedia exercise content may include the UI 710 including the exercise completion message such as "XX, thank you for your effort". However, the exercise completion message included in the UI 710 is merely an example, and other exercise completion messages may be included in the UI 710.

Start and end of reproduction of the multimedia exercise content may be controlled according to the exercise information of the user. For example, when the user initially starts to exercise and then an exercise amount of the user exceeds a preset third exercise amount (for example, 5 Kcal), the server 200 starts to reproduce the multimedia exercise content. When the exercise amount of the user exceeds a preset fourth exercise amount (for example, 200 Kcal), the server 200 may stop reproducing the multimedia exercise content.

Therefore, as described above, the server 200 provides the lively and active multimedia exercise content to the user according to the exercise information and physical information of the user so that it is possible for the user to enjoy the multimedia exercise content interestingly and actively.

In the above-described exemplary embodiment, the example in which the multimedia apparatus 300 receives the multimedia exercise content from the server and outputs the received multimedia exercise content has been described, but this is merely an example. The multimedia apparatus 300 may have the function of the server 200 and directly execute the multimedia exercise content.

For example, the control unit 390 acquires the exercise information from the exercise information acquisition unit 330 while executing the multimedia exercise content, the control unit 390 may adjust the screen change rate of the video data included in the multimedia exercise content according to the exercise information. For example, when the exercise amount is large, the control unit 390 may process the multimedia exercise content to increase the screen change rate of the video data. When the exercise amount is small, the control unit 390 may process the multimedia exercise content to reduce the screen change rate of the video data.

The control unit 390 may determine the recommended exercise criterion corresponding to the physical information input by the user, and compare the exercise information with the recommended exercise criterion when the exercise information is acquired from the exercise information acquisition unit 330. At this time, the recommended exercise criterion may be calculated based on the physical information (for example, age, weight, height, sex, and the like of the user) of the user and health-related information (for example, basic physical strength information, disease present/absence, and the like) of the user.

When the exercise information does not match the recommended exercise criterion, the control unit 390 may adjust the screen change rate of the video data included in the multimedia exercise content so that the exercise information matches the recommended exercise criterion. When the input exercise information is equal to or less than a preset value with respect to the recommended exercise criterion, the control unit 390 may process the multimedia exercise content to increase a screen change rate of currently output video data. When the input exercise information exceeds the preset value with respect to the recommended exercise criterion, the control unit 390 may process the multimedia exercise content to reduce the screen change rate of the currently output video data.

The control unit 390 may, in one exemplary embodiment, directly generate the UIs shown in FIGS. 4 to 7 according to the exercise information of the user and display the generated UIs. For example, when the exercise information does not match the recommended exercise criterion, the control unit 390 may display the UI 510 including the guidance message for guiding the exercise information corresponding to the recommended exercise criterion as shown in FIG. 5. When the exercise amount exceeds a preset second threshold value, the control unit 390 may display the UI 610 including the cheering message as shown in FIG. 6. Further, when the exercise amount exceeds a preset third threshold value, the control unit 390 may display the UI 710 including the exercise completion message as shown in FIG. 7. The control unit 390 may display the exercise information acquired by the exercise information acquisition unit 330 together with the video data of the multimedia exercise content.

The multimedia apparatus 300 according to the above-described exemplary embodiment can provide the lively and active multimedia exercise content to the user using the exercise information and physical information of the user.

Hereinafter, a method of providing a multimedia exercise content using the server 200 will be described with reference to FIGS. 8 and 9.

Figure 8:
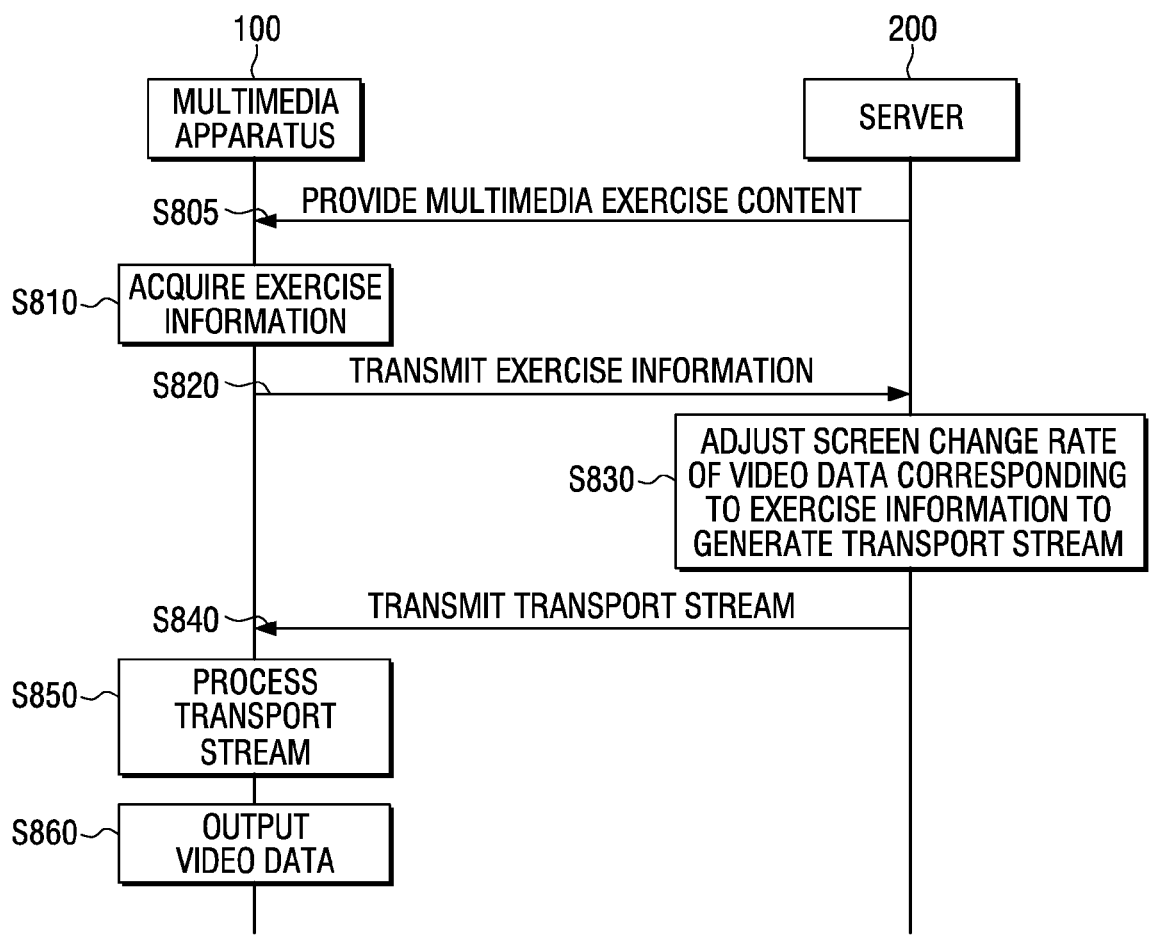
FIG. 8 is a sequence diagram illustrating a method of providing a multimedia exercise content using a multimedia and a server according to an exemplary embodiment of the present invention.

FIG. 8 is a sequence diagram illustrating a method of providing a multimedia exercise content using a multimedia apparatus and a server according to an exemplary embodiment.

Referring to FIG. 8, the server 200 provides multimedia exercise content to the multimedia apparatus 100 in step S805. The multimedia exercise content may include video data (for example, a background screen such as a trail, a strolling alley, and the like) and audio data (for example, music, a guidance message, and the like).

The multimedia apparatus 100 acquires exercise information from the user while receiving the multimedia exercise content from the server 200 in step S810. For example, the multimedia apparatus 100 may acquire the exercise information of the user using various capturing units and sensors. The exercise information may include at least one factor such as an exercise amount, an exercise period, an exercise speed, an exercise distance, a pulse rate, and a change in a weight of the user. However, it is noted that the exercise information may include other types of factors.

The multimedia apparatus 100 transmits the acquired exercise information to the server 200 through the communication unit 130 in step S820.

The server 200 adjusts a screen change rate of the video data to correspond to the received exercise information and generates a transport stream for the multimedia exercise content in step S830. When an exercise amount is large, the server 200 processes the video data to increase the screen change rate of the video data. When the exercise amount is small, the server 200 processes the video data to reduce the screen change rate of the video data.

Then, the server 200 transmits the generated transport stream to the multimedia apparatus 100 in step S840.

The multimedia apparatus 100 processes the received transport stream in step S850, and outputs the video data included in the multimedia exercise content in step S860.

As described above, multimedia exercise content according to the exercise information is provided using the server 200 and the multimedia apparatus 100 so that it is possible to provide the lively and active multimedia exercise content to the user.

Figure 9:
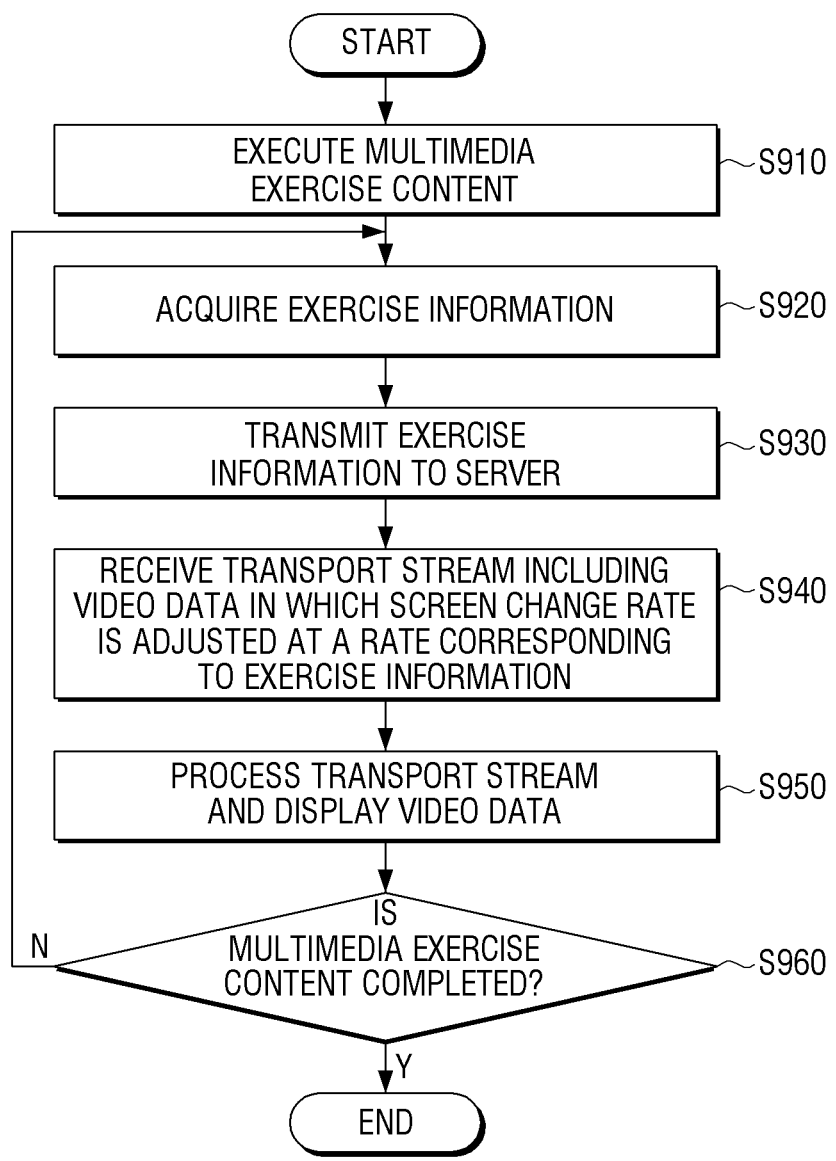
FIG. 9 is a flowchart illustrating a method of providing an exercise content by a multimedia apparatus according to an exemplary embodiment of the present invention.

FIG. 9 is a flowchart illustrating a method of providing multimedia exercise content by a multimedia apparatus using a server.

Referring to FIG. 9, the multimedia apparatus 100 executes multimedia exercise content in step S910. That is, the multimedia apparatus 100 receives the multimedia exercise content from the server 200, performs signal processing on the received multimedia exercise content, and provides the signal-processed result to the user.

Then, the multimedia apparatus 100 acquires exercise information of the user in step S920. The exercise information of the user may be acquired through various capturing units and sensors and the exercise information of the user may include information such as an exercise amount, an exercise distance, exercise speed, an exercise period, a pulse rate, and a change in a temperature. However, it is noted that the exercise information is not limited to the examples noted above.

The multimedia apparatus 100 transmits the exercise information to the server 200 in step S930.

Then, the multimedia apparatus 100 receives a transport stream including video data in which a screen is changed at a rate corresponding to the exercise information from the server 200 in step S940. At this time, the video data included in the multimedia exercise content has a fast screen change rate as the exercise amount is large (for example, when the exercise speed is fast or when calorie consumed per hour is large), and has a slow screen change rate when the exercise amount is small (for example, when the exercise speed is slow or when calorie consumed per hour is small).

The multimedia apparatus 100 processes the transport stream and displays the video data in step S950.

The multimedia apparatus 100 determines whether or not a completion command for the multimedia exercise content is input in step S960. When determined that the completion command is not input (S960—N), the process proceeds to step S920 and then the above-described processes step S920 to step S950 are re-performed. When it is determined that the completion command is input (S960—Y), the multimedia apparatus 100 stops executing the multimedia exercise content.

As described above, the multimedia apparatus 100 provides the video data, in which the screen change rate is adjusted according to the exercise information using the server, to the user, and thus it is possible for the user to enjoy the lively and active multimedia exercise content.

Figure 10:
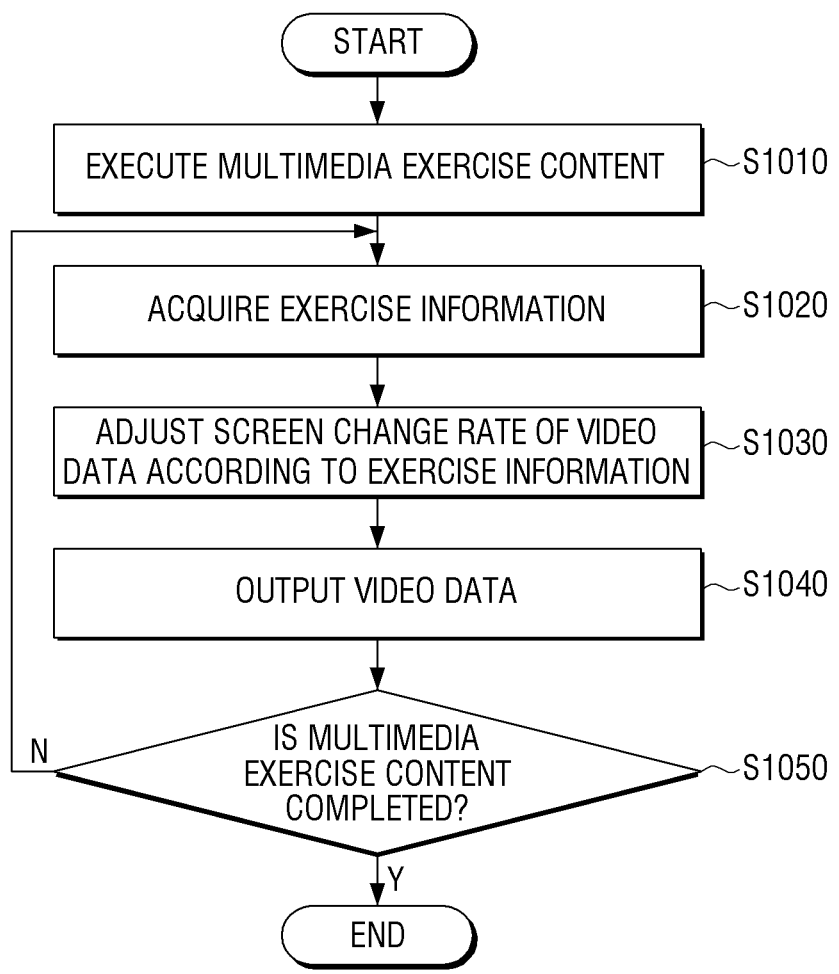
FIG. 10 is a flowchart illustrating a method of providing exercise content by a multimedia apparatus according to an exemplary embodiment of the present invention.

FIG. 10 is a flowchart illustrating a method of adjusting a screen change rate of video data by the multimedia apparatus 100 according to another exemplary embodiment.

Referring to FIG. 10, the multimedia apparatus 100 executes multimedia exercise content in step S1010.

The multimedia apparatus 100 acquires exercise information of a user in step S1020. The exercise information of the user may be acquired through various capturing units and sensors and the exercise information of the user may include information such as an exercise amount, an exercise distance, exercise speed, an exercise period, a pulse rate, and a change in temperature.

Then, in step S1030, the multimedia apparatus 100 adjusts a screen change rate of video data included in the multimedia exercise content according to the exercise information. At this time, the multimedia apparatus 100 may process the multimedia exercise content to increase the screen change rate of the video data when the exercise amount of the user is larger than a predetermined amount, while the multimedia apparatus 100 may process the multimedia exercise content to reduce the screen change rate of the video data when the exercise amount is smaller than a predetermined amount.

The multimedia apparatus 100 outputs the video data in which the screen change rate is adjusted in step S1040.

Then, in step S1050, the multimedia apparatus 100 determines whether or not a completion command for the multimedia exercise content is input. When determined that the completion command is not input at step S1050—N, the process proceeds to step S1020 and the above-described processes step S1020 to step S1040 are re-performed. When determined that the completion command is input at step S1050—Y, the multimedia apparatus 100 stops executing the multimedia exercise content.

As described above, the multimedia apparatus 100 has the function of the server 200, and can adjust the screen change rate of the video data according to the exercise information of the user, making it possible for the user to enjoy the lively and active multimedia exercise content using only the multimedia apparatus 100.

In addition, a program code for executing the display methods according to the above-described various exemplary embodiments may be recorded in various types of non-transitory recording media. Specifically, the program code for executing the display methods may be stored in various types of non-transitory recording media readable by a terminal such as a Random Access Memory (RAM), a flash memory, a Read Only Memory (ROM), an Erasable Programmable ROM (EPROM), an Electronically Erasable and Programmable ROM (EEPROM), a register, a hard disc, a removable disc, a memory card, a USB memory, a Compact Disc ROM (CD-ROM).

The foregoing exemplary embodiments and advantages are merely exemplary and are not to be construed as limiting the present inventive concept. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A display method of a multimedia apparatus, the display method comprising:
    acquiring exercise information of a user through at least one of a camera and a sensor of the multimedia apparatus;
    transmitting the exercise information of the user to a server;
    receiving from the server a transport stream comprising video data in which a screen is changed at a rate corresponding to the exercise information;
    only when the exercise information of the user does not match a recommended exercise criterion corresponding to physical information of the user, receiving reference video data in which the screen is changed at a rate corresponding to the recommended exercise criterion;
    displaying the video data on a display unit of the multimedia apparatus by processing the transport stream when the exercise information of the user matches the recommended exercise criterion corresponding to the physical information of the user; and
    displaying the reference video data on the display unit only when the exercise information of the user does not match the recommended exercise criterion corresponding to the physical information of the user,
    wherein the reference video data is displayed consistently when the exercise information of the user does not match the recommended exercise criterion.

2. The display method as claimed in claim 1, wherein the exercise information of the user includes an exercise speed, and a screen change rate is adjusted in proportion to the exercise speed.

3. The display method as claimed in claim 1, further comprising:
    storing the physical information of the user;
    determining the recommended exercise criterion corresponding to the physical information of the user;
    comparing the exercise information of the user with the recommended exercise criterion when the exercise information of the user is acquired; and
    displaying a guidance message for the recommended exercise criterion when the exercise information of the user does not match the recommended exercise criterion.

4. The display method as claimed in claim 1, further comprising receiving from the server and displaying a guidance message for the recommended exercise criterion when the exercise information of the user does not match the recommended exercise criterion corresponding to the physical information of the user.

5. The display method as claimed in claim 1, further comprising:
    outputting first audio data corresponding to the video data; and
    converting the first audio data into second audio data and outputting the second audio data when an exercise amount included in the exercise information of the user exceeds a preset first threshold value.

6. The display method as claimed in claim 1, further comprising outputting a User Interface (UI) comprising a cheering message when an exercise amount included in the exercise information of the user exceeds a preset second threshold value.

7. The display method as claimed in claim 1, further comprising displaying a User Interface (UI) comprising the exercise information of the user together with the video data.

8. The display method as claimed in claim 1, further comprising outputting a User Interface (UI) comprising an exercise completion message when an exercise amount included in the exercise information of the user exceeds a preset third threshold value.

9. The display method as claimed in claim 1, wherein the server is provided in the multimedia apparatus.

10. A multimedia apparatus providing multimedia exercise content, the multimedia apparatus comprising:
    an exercise information acquisition unit configured to acquire exercise information of a user through at least one of a camera and a sensor;
    a communication unit configured to perform communication with a server;
    a display unit; and
    a processor configured to execute program code comprising instructions to:
        control the communication unit to transmit the exercise information of the user to the server,
        receive from the server a transport stream comprising video data in which a screen is changed at a rate corresponding to the exercise information of the user and
        receive, only when the exercise information of the user does not match a recommended exercise criterion corresponding to physical information of the user, a transport stream comprising reference video data in which the screen is changed at a rate corresponding to the recommended exercise criterion,
        control the display unit to display the video data by processing the transport stream when the exercise information of the user matches the recommended exercise criterion corresponding to the physical information of the user, and
        control the display unit to display the reference video data by processing the transport stream only when the exercise information of the user does not match the recommended exercise criterion corresponding to the physical information of the user,
    wherein the processor is further configured to control the display unit to display the reference video data consistently when the exercise information of the user does not match the recommended exercise criterion.

11. The multimedia apparatus as claimed in claim 10, wherein the exercise information of the user comprises exercise speed, and a screen change rate is adjusted in proportion to the exercise speed.

12. The multimedia apparatus as claimed in claim 10, further comprising a storage unit configured to store the physical information of the user,
    wherein the program code further comprises instructions to:
        determine the recommended exercise criterion corresponding to the physical information of the user,
        compare the exercise information of the user with the recommended exercise criterion when the exercise information of the user is acquired, and
        control a guidance message for the recommended exercise criterion to be displayed on the display unit when the exercise information of the user does not match the recommended exercise criterion.

13. The multimedia apparatus as claimed in claim 10, wherein the program code further comprises instructions to:
receive a guidance message for the recommended exercise criterion from the server via the communication unit when the exercise information of the user does not match the recommended exercise criterion corresponding to the physical information of the user, and
control the received guidance message to be displayed on the display unit.

14. The multimedia apparatus as claimed in claim 10, further comprising an audio output unit configured to output first audio data corresponding to the video data,
wherein the program code further comprises instructions to control the audio output unit to convert the first audio data into second audio data and output the second audio data when an exercise amount included in the exercise information of the user exceeds a preset first threshold value.

15. The multimedia apparatus as claimed in claim 10, wherein the program code further comprises instructions to output a User Interface (UI) comprising a cheering message when an exercise amount included in the exercise information of the user exceeds a preset second threshold value.

16. The multimedia apparatus as claimed in claim 10, wherein the program code further comprises instructions to control a User Interface (UI) comprising the exercise information of the user to be displayed on the display unit together with the video data.

17. The multimedia apparatus as claimed in claim 10, wherein the program code further comprises instructions to output a User Interface (UI) comprising an exercise completion message when an exercise amount included in the exercise information of the user exceeds a preset third threshold value.

18. The multimedia apparatus as claimed in claim 10, wherein the server is provided in the multimedia apparatus.

* * * * *